United States Patent
Pletsch et al.

(10) Patent No.: US 9,988,333 B2
(45) Date of Patent: Jun. 5, 2018

(54) PROCESS FOR MAKING 2,5-DIHALOGENATED PHENOL

(71) Applicant: BASF SE, Ludwigshafen (DE)

(72) Inventors: Andreas Pletsch, Limburgerhof (DE); Nicole Holub, Mannheim (DE); Thomas Ulrich, Olten (CH); Petr Kvita, Reinach (CH); Laurent Cavin, Frenkendorf (CH)

(*) Notice: Subject to any disclaimer, the term of this patent is extended or adjusted under 35 U.S.C. 154(b) by 0 days. days.

(21) Appl. No.: 15/311,951

(22) PCT Filed: May 18, 2015

(86) PCT No.: PCT/EP2015/060895
§ 371 (c)(1),
(2) Date: Nov. 17, 2016

(87) PCT Pub. No.: WO2015/177093
PCT Pub. Date: Nov. 26, 2015

(65) Prior Publication Data
US 2017/0174603 A1    Jun. 22, 2017

(30) Foreign Application Priority Data
May 19, 2014   (EP) .................................. 14168877

(51) Int. Cl.
| C07C 37/01  | (2006.01) |
| C07C 51/353 | (2006.01) |
| C07C 37/045 | (2006.01) |
| C07C 37/76  | (2006.01) |
| C07C 241/02 | (2006.01) |
| C07C 209/36 | (2006.01) |
| C07C 201/08 | (2006.01) |
| C07C 51/00  | (2006.01) |
| C07C 67/00  | (2006.01) |

(52) U.S. Cl.
CPC .......... *C07C 51/353* (2013.01); *C07C 37/045* (2013.01); *C07C 37/76* (2013.01); *C07C 51/00* (2013.01); *C07C 67/00* (2013.01); *C07C 201/08* (2013.01); *C07C 209/365* (2013.01); *C07C 241/02* (2013.01)

(58) Field of Classification Search
USPC ............................................ 560/65; 568/777
See application file for complete search history.

(56) References Cited

U.S. PATENT DOCUMENTS

| 2,799,714 A | 7/1957 | Dugan |
| 3,013,054 A | 12/1961 | Richter |
| 3,399,034 A * | 8/1968 | Genas .................. C01B 21/086 423/388 |
| 3,726,929 A | 4/1973 | Milnes |
| 4,005,151 A | 1/1977 | Wataya et al. |
| 4,094,913 A | 6/1978 | Carlson |
| 4,161,611 A | 7/1979 | Kim |
| 4,232,172 A | 11/1980 | Becher |

FOREIGN PATENT DOCUMENTS

| CN | 102516072 A |   | 6/2012 |
| CN | 102838457   |   | 12/2012 |
| CN | 102125035   | * | 7/2013 |
| CN | 102295552 B | * | 9/2013 |
| DE | 2509407     |   | 9/1975 |
| DE | 3512877 C1  |   | 11/1986 |
| GB | 1404435 A   |   | 8/1975 |

(Continued)

OTHER PUBLICATIONS

Lin et al. Organic & Biomolecular Chemistry (2004), 2(18), 2624-2629.*

(Continued)

*Primary Examiner* — Sudhakar Katakam
*Assistant Examiner* — Ana Z Muresan
(74) *Attorney, Agent, or Firm* — Brinks Gilson & Lione

(57) ABSTRACT

The present invention relates to a process for reacting chemical compounds comprising the step of reacting a compound of formula (IV)

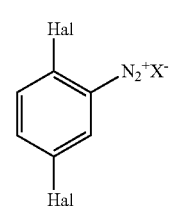

IV wherein Hal is independently selected from Cl or Br, and $X^-$ is a monovalent anion, in the presence of an inorganic acid, wherein the aqueous inorganic acid has a concentration of at least about 60%, at a temperature of about 140° C. to about 250° C., to obtain a compound of formula (V)

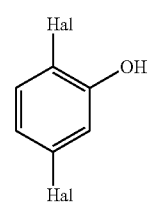

V wherein Hal is as defined above.

15 Claims, No Drawings

(56) References Cited

FOREIGN PATENT DOCUMENTS

| JP | 1149715 A2 | 6/1989 |
|---|---|---|
| WO | 200183417 A1 | 11/2001 |
| WO | WO 2015049160 | 4/2014 |
| WO | WO 2015049360 | 4/2014 |
| WO | WO 2015067494 | 5/2015 |
| WO | WO 2015082415 | 6/2015 |
| WO | WO 2015082422 | 6/2015 |
| WO | WO 2015086698 | 6/2015 |
| WO | WO 2015095284 | 6/2015 |
| WO | WO 2015124651 | 8/2015 |

OTHER PUBLICATIONS

Machine translation for CN102295552.*
Machine translation for CN 102125035.*
International Search Report, issued in PCT/EP2015/060895, dated Jul. 23, 2015.
Finger et al., "Aromatic Fluorine Compounds. VIII. Plant Growth Regulators and Intermediates," Journal of The American Chemical Society, vol. 81, (1959), pp. 94-101, Search Report.
International Preliminary Report on Patentability, issued in PCT/EP2015/060895, dated Nov. 22, 2016.
Search Report, issued in EP Application No. 14168877.0, dated Oct. 30, 2014.
Office Action, issued in co-pending U.S. Appl. No. 15/026,878, dated Dec. 11, 2017.
Holleman, "Les Trois Trichlorobenzenes et Leur Reaction avec le Methylate de Sodium," Recueil des Travaux Chimiques des Pays-Bas et de la Belique, vol. 37, (1918), pp. 195-204 (XP-002723298).
Holleman, M.A.F., "Les trois trichorobenzenes et leur reaction avea le methylate de sodium", Recueil des travaux chimiques des pays-bas et de la belique, 1918, p. 195-204, vol. 37.
Testaferri, L., et al., "The reactions of unactivated aryl halides with sodium methoxide in HPMA", Tetrahedron, 1983, p. 193-197, vol. 29, No. 1.
Kraay, G.M. "L'action du methylate de sodium sur quelques derivres de l'orthodichlorobenzene" Recueil des travaux chimiques des pays-bas, Elsevier Science Publishers, Jan. 1931, p. 753-792, vol. 50.
Smith, M.S. et al., "March's Advanced Organic Chemistry" 5th Edition, 2001, p. 860-861, John Wiley & Sons, Inc. , New York, USA.

Noelting et al., "Zur Kenntniss des Amido-p-dichlorbenzols," Berichte der Deutschen Chemischen Gesellschaft, (1905), p. 3506.
Cresp et al., "Synthesis of Piloquinone, a Metabolite of Streptomyces Pilosus Ettlinger," Journal of the Chemical Society, 1974, pp. 2435-2447.
Schmitz et al., "Ortho-Specific Bromination of Phenols," Journal für praktische Chemie, 1985, vol. 327, No. 6, pp. 998-1006.
Decrauw, TH. "The principle of induced alternating polarity in connection with the reacions of derivatives of p-dichlorobenzene and other compounds with sodium methylate", Recueil des travaux chimiques des pays-Bas, Elsevier science Publishes. Amerdam, NL, Jan. 1, 1931, vol. 50, p. 753-792.
Ouellet, S. et al., "Regioselective SNAr reactions of substituted diflourobenzene derivatives: practical synthesis of fluoroaryl ethers and substituted resorcinols", Tetrahedron Letters, Jul. 8, 2009, p. 3776-3779, vol. 50, No. 27.
Shan et al., "Pd-Catalyzed C-H Oxygenation with TFA/TFAA: Expedient Access to Oxygen-Containing Heterocycles and Late-Stage Drug Modification," Angew. Chem. Int. Ed., vol. 51, (2012), pp. 13070-13074.
Verloop et al., "Use of Linear Free Energy Related and Other Parameters in the Study of Fungicidal Selectivity," Pesticide Science, vol. 7, No. 4, (1976), pp. 379-390.
Li et al., "Pd(OAc)2-Catalyzed Alkoxylation of Arylnitriles via sp2 C—H Bond Activation Using Cyano as the Directing Group," The Journal of Organic Chemistry, vol. 77, No. 18, (2012), pp. 8362-8366.
Zhang et al., "Pd(II)-Catalyzed Hydroxylation of Arenes with 1 atm of O2 or Air," Journal of the American Chemical Society, vol. 131, No. 41, (2009), pp. 14654-14655.
Li et al., "Preparation of Monofluorophenols via the Reaction of Difluorobenzene Derivatives with Potassium Trimethylsilanoate," SynLett, vol. 2009, No. 4, (2009), pp. 633-637.
Hashimoto et al., "Hydrolysis of 1,2,4-Trichlorobenzene," The Doshisha Engineering Review, vol. 8, No. 2, (1957), pp. 76-79.
Methoxide Catalysts in Biodiesel Production, (2012), retrieved from http://articles.extension.org/pages/26615/methoxide-catalysts-in-biodiesel-production, pp. 1-3.
Office Action, issued in co-pending U.S. Appl. No. 15/102,353, dated Oct. 24, 2017.
Office Action, issued in co-pending U.S. Appl. No. 15/026,878, dated Jan. 9, 2017.
Final Office Action, issued in co-pending U.S. Appl. No. 15/026,878, dated May 24, 2017.

* cited by examiner

PROCESS FOR MAKING 2,5-DIHALOGENATED PHENOL

This application is a National Stage application of International Application No. PCT/EP2015/060895, filed May 18, 2015. This application also claims priority under 35 U.S.C. § 119 to European Patent Application No. 14168877.0, filed May 19, 2014.

The present invention relates to a process for providing 2,5-dihalogen substituted phenol derivatives. Preferably, the 2,5-dihalogen substituted phenol derivative is continuously removed from the reaction system using water steam distillation. The inventive process can in a preferred embodiment be employed for obtaining 2,5-dichlorophenol, which is an important intermediate in the production of the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid. It is expected that the global demand for dicamba will increase significantly.

Dicamba is typically produced on an industrial scale from 2,5-dichlorophenol using carboxylation under Kolbe-Schmitt conditions, methylation and subsequently saponification/acidification. 2,5-dichorophenol in turn can be obtained from 1,4-dichlorobenzene or 1,2,4-trichlorobenzene. The synthetic route via 1,2,4-trichlorobenzene suffers from limited availability of this compound and from the formation of several by-products which are formed in the synthesis of 2,5-dichlorophenol. The synthetic route via 1,4-dichlorobenzene involves nitration, reduction to 2,5-dichloroaniline, diazotation, and subsequent conversion of the diazonium salt to 2,5-dichlorophenol. However, due to the reactivity of the diazonium salt several by-products are also formed in the latter step so that the yield thereof is undesirably low. In addition, on an industrial scale major amounts of waste material are generated in this step.

Prior art processes for obtaining 2,5-dihalogen phenols, such as 2,5-dichlorophenol, from 2,5-dihalogen aniline are typically carried out batch-wise by heating the diazonium salt in an aqueous acid. Illustrative reaction conditions are e.g. described in DE 25 09 407. In conventional processes, the diazonium salt is typically not heated to temperatures higher than 140° C. The obtained yields are about 70%

In view of the above, there is a need in the art for an improved process for obtaining 2,5-dihalogen substituted phenols, such as 2,5-dichlorophenol. In particular, there is a special need in the art for processes providing 2,5-dihalogen substituted phenols in better yields. Furthermore, there is a need for such processes providing increased yield that advantageously can be carried out on an industrial scale. Moreover, such processes should preferably allow for the reduction of waste material and/or for recyclability of materials applied.

The object of the present invention is to meet the above needs. In particular, one object of the present invention is to provide an improved process for obtaining 2,5-dihalogen substituted phenols such as 2,5-dichlorophenol. The process according to the present invention can be carried out on an industrial scale. Furthermore, in a preferred embodiment, the process according to the present invention produces less waste material and allows for the recycling of at least part of the chemicals or materials involved in the process. In an especially preferred embodiment, the object of the present invention is the provision of a process for providing 2,5-dichlorophenol and finally dicamba on an industrial scale in good yields.

SUMMARY OF THE INVENTION

The present invention relates to a process for reacting chemical compounds comprising the step of reacting a compound of formula (IV)

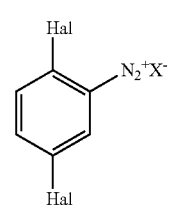

IV wherein Hal is independently selected from Cl or Br, and $X^-$ is a monovalent anion, in the presence of an aqueous inorganic acid, wherein the aqueous inorganic acid has a concentration of at least about 60%, at a temperature of about 140° C. to about 250° C., to obtain a compound of formula (V)

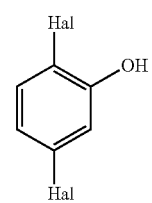

V wherein Hal is as defined above.

The process of the present invention may provide an increased yield of 2,5-dihalogen phenol. The inventors of the present invention have found that higher yields can be obtained by carrying out hydrolysis of the 2,5-dihalogen diazonium salt of formula (IV) to obtain the 2,5-dihalogen phenol of formula (V) at higher temperatures in a highly acidic medium.

Furthermore, in some preferred embodiments the resulting product of formula (V) is continuously removed from the reaction system using water steam distillation. By continuous removal of the product from the reaction mixture, less by-products (e.g. insoluble resins) are formed, and thus the yield may further be increased. The present inventors have further found that water steam distillation can advantageously be used for removing the 2,5-dihalogen phenol from the reaction system.

The inorganic acid applied in the above process is e.g. selected from the group consisting of $H_2SO_4$, HCl, HBr, and $H_3PO_4$. In a more preferred embodiment, the inorganic acid is $H_2SO_4$. In these cases it is advantageous e.g. from the viewpoint of recycling the acid after completion of the reaction, that the preceding diazotation step is also carried out using $H_2SO_4$ as the acid. Thus, the a preferred embodiment, the present invention relates to a process as defined above, wherein $X^-$ is $HSO_4^-$, and $H_2SO_4$ is employed as the inorganic acid in the diazonium salt hydrolysis step. In a further preferred embodiment, the concentration of the H₂SO₄ in the diazonium salt hydrolysis step is at least about 65%, more preferably at least about 70%. In another preferred embodiment, the concentration of the H₂SO₄ in the diazonium salt hydrolysis step is about 60% to about 85%, more preferably about 70% to about 75%. Most preferably, the concentration of the H₂SO₄ in the diazonium salt hydrolysis step is about 72%. In case the diazonium salt hydrolysis product is continuously removed from the reaction mixture, concentrations of the H₂SO₄ greater than about 70%, e.g. about 72% to about 75%, are preferred.

In a further preferred embodiment, the present application relates to a process as defined above, wherein H₂SO₄ is used as the inorganic acid and wherein the H₂SO₄ is at least in part recycled. This procedure allows for reduction of waste and thus a more economical process.

As outlined above, the diazonium salt hydrolysis step is carried out at higher temperatures, i.e. at a temperature of about 140° C. to about 250° C. The inventors of the present invention have found that the better yields are obtained in the diazonium salt hydrolysis step when the temperature at which this step is performed is higher (i.e. above about 140° C.), in particular when the resulting reaction product is continuously removed from the reaction system in a suitable way. Thus, in a preferred embodiment, the above process is carried out at a temperature of at least about 150° C., more preferably at least about 160° C., and still more preferably about 170° C. In another preferred embodiment, the diazonium salt hydrolysis step is carried out at a temperature of about 150° C. to about 190° C., more preferably about 170° C. to about 180° C.

According to the present invention the diazonium salt of formula (IV) can be obtained in any suitable way. Typically, the compound of formula (IV) is provided by diazotating a compound of formula (III)

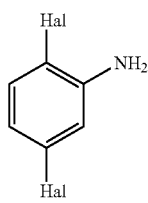

III wherein Hal is as defined above.

Suitable reaction conditions for obtaining the compound of formula (IV) from 2,5-dihalogen substituted anilines of formula (III) are well known in the art. Typically, the compound of formula (III) is dissolved in an aqueous medium comprising an inorganic acid, such as H₂SO₄ or HCl, and a diazotating agent is added. Suitable diazotating agents include, but are not limited to an alkali metal nitrite such as NaNO₂, nitrous acid (HNO₂) or NOHSO₄. In a preferred embodiment of the present invention, the step of diazotating the compound of formula (III) to obtain the compound of formula (IV) is carried out in H₂SO₄. In a further preferred embodiment the H₂SO₄ used as the acid in the diazotating step has a concentration of at least about 40%.

In some embodiments according to the present invention, diazotation is carried out under highly concentrated conditions. Thus, in preferred embodiments, a molar ratio of H₂SO₄ to the compound of formula (III) is about 6:1 or lower, preferably about 5:1 or lower, such as about 4:1 to about 3:1 is employed.

Furthermore, the preferred diazotating agent used according to the invention is NOHSO₄. The present inventors have found that a particular advantage of using NOHSO₄ as the diazotating agent is that also the step of providing the compound of formula (IV) can be carried out continuously. Typically, about 0.95 to about 1.2 molar equivalents of NOHSO₄ are used based on the molar amount of 2,5-dihalogen aniline of formula (III). In a preferred embodiment, about 0.96 to about 1.0 molar equivalents of NOHSO₄, more preferably about 0.98 molar equivalents of NOHSO₄, per one molar equivalent of 2,5-dihalogen aniline of formula (III) is employed. NOHSO₄ can be provided as an aqueous solution, e.g. an aqueous solution having a concentration of about 20% to about 60%, preferably 30% to about 50%, such as 35% to 45%.

In another embodiment, NOSO₄ is provided by feeding NO$_x$ gas to sulfuric acid preferably having a concentration of at least about 60%. In this way, concentrated sulfuric acid already containing diazotating agent and suitable as reaction medium according to the present invention in the subsequent reaction step can be obtained. In an advantageous embodiment, the NO$_x$ gas stream is taken from nitrogen oxide containing exhaust gas. Thus, NO$_x$ exhaust gas already available on a chemical reaction plant can be put to suitable use avoiding the generation of harmful waste material. In a preferred embodiment, such NO$_x$ gas is a mixture of NO and NO₂ in a molar ratio of about 1:1.

The temperature for carrying out the diazotating step can be varied widely. For example, the reaction can be performed at low temperature, such as e.g. about −5° C. or about 0° C., or at elevated temperatures, such as e.g. up to about 80° C. In a preferred embodiment, the step of diazotating the compound of formula (III) to obtain the diazonium salt of formula (IV) is carried out at a temperature of about 45° C. to about 65° C., preferably about 50° C. to about 60° C.

In a preferred embodiment, the 2,5-dihalogen phenol of formula (V) produced in the inventive process is continuously removed from the reaction system. The present inventors have found that the yields obtained in the diazonium salt hydrolysis step can be significantly increased when the resulting product of formula (V) is continuously removed. The present inventors have further found that steam distillation is a suitable and advantageous method for removing the compound of formula (V) from the reaction system. In this way, the process can be carried out continuously. A further advantage is that the water used for steam distillation can be recycled so that less waste material is generated in the process. Thus, in a preferred embodiment, the present invention provides a process as defined above, wherein at least part of the water used for steam distillation is recycled in a closed water loop.

The compound of formula (III) used in preferred embodiments of the invention for obtaining the diazonium salt of formula (IV) can be provided in various ways as known in the art. Typically, the compound of formula (III) is obtained by reducing a compound of formula (II)

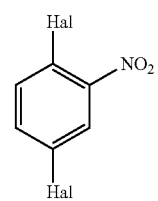

II wherein Hal is as defined above. Illustrative reaction conditions include e.g. hydrogenation in the presence of various metal catalysts, such as ferrous chloride, at elevated temperatures, such as about 200° C. to about 300° C.

The compound of formula (II) employed in preferred embodiments of the present invention can be obtained in various ways as known in the art. Typically, the compound of formula (II) is obtained by nitrating a compound of formula (I)

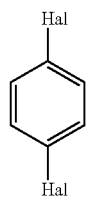

I wherein Hal is as defined above. The reaction is typically performed in a concentrated inorganic acid such as $H_2SO_4$ in admixture with concentrated nitric acid.

In preferred embodiments according to the present invention, the above compound of formula (V) is further converted to other useful intermediates and/or end products. In one preferred embodiment, the compound of formula (V) is reacted to obtain a compound of formula (VI)

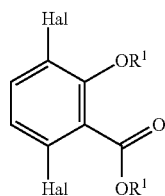

VI wherein Hal is as defined above, and $R^1$ is an alkali metal.

The above reaction from compounds of formula (V) to compounds of formula (VI) is known in the art as the "Kolbe-Schmitt reaction". Reactions under Kolbe-Schmitt conditions can be carried out on an industrial scale in good yields. For example, the above conversion is part of known reaction sequences for obtaining dicamba from 2,5-dichlorophenol. The step is typically carried out in the presence of an alkali metal hydroxide and carbon dioxide.

In an additional preferred embodiment, the process of the invention further comprises the step of reacting the compound of formula (VI) to obtain an ether of formula (VII)

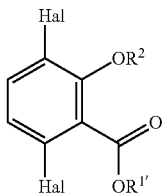

VII wherein $R^2$ is —$(C_1-C_4)$alkyl, $R^{1'}$ is an alkali metal or —$(C_1-C_4)$alkyl, and Hal is as defined above. This reaction step is also carried out in prior art reaction sequences for obtaining dicamba. Since dicamba is a preferred end product according to the present invention, and dicamba contains a free carboxylic acid group, it is not relevant in these preferred embodiments that in the reaction the carboxylic acid group is partly converted to the corresponding ester and partly remains in neutralized form.

Rather, in preferred embodiments according to the invention, the resulting product of formula (VII) is converted to the corresponding neutralized carboxylic acid by hydrolyzing an ester of formula (VII) (i.e. wherein $R^{1'}$ is —$(C_1-C_4)$ alkyl) under basic conditions, and is subsequently acidified to obtain a compound of formula (VIII)

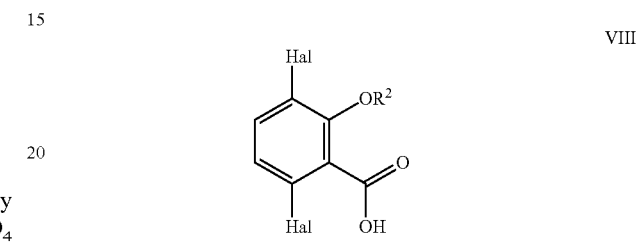

VIII wherein $R^2$ and Hal are as defined above. The above reaction step can be carried out analogously to prior art reactions sequences for obtaining dicamba from 2,5-dichlorophenol in good yields on an industrial scale.

In especially preferred embodiments according to the present invention, Hal is Cl. $R^1$ is preferably selected from Na or K. $R^1$ is derived from an alkali metal hydroxide, i.e. sodium hydroxide or potassium hydroxide used during the Kolbe-Schmitt reaction step. It may further be advantageous to replace one alkali metal with another alkali metal in preferred embodiments of the invention as described below. In a preferred embodiment, $R^1$ is K in the above-described Kolbe-Schmitt reaction step, i.e. KOH is used in the step of providing the compound of formula (VI).

In further preferred embodiments according to the present invention, in case $R^{1'}$ is not an alkali metal in the compound of formula (VII) described above, $R^{1'}$ is ethyl or methyl. In these cases, $R^{1'}$ is identical to $R^2$. $R^2$ is, according to preferred embodiments, also selected from ethyl and methyl. In a more preferred embodiment, $R^2$ is methyl, thus also $R^{1'}$ is more preferably methyl in case it is not an alkali metal. In case $R^{1'}$ is an alkali metal, it may be identical to $R^1$ as defined above, or preferably is an alkali metal different from $R^1$, i.e. can be different in different reaction steps. For example, $R^{1'}$ may be Na or may be identical to $R^2$.

In especially preferred embodiments, the processes according to the present invention are employed for obtaining dicamba. In these preferred embodiments, the compound of formula (VIII) is

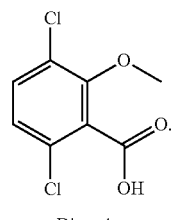

Dicamba

DETAILED DESCRIPTION OF THE INVENTION

In the following, illustrative embodiments of the present invention are described in more detail.

The term "alkali metal" when used in the context of the present invention refers to lithium, sodium or potassium. Sodium and potassium are preferred.

Reference to the concentration of a solution or an acid, in particular aqueous solution or acid, given in percent refers in the context of the present invention to the mass of compound or acid per mass of aqueous solution. For example, aqueous sulfuric acid ($H_2SO_4$) having a concentration of 60% means a concentration obtained by combining 60 g of $H_2SO_4$ with 40 g of water.

The present invention relates to a process for reacting a compound of formula (IV) to obtain a compound of formula (V)

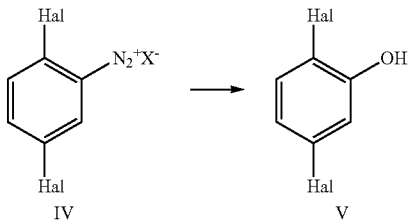

According to the present invention, Hal is independently selected from Cl and Br. In preferred embodiment of the invention, Hal is Cl.

The monovalent anion $X^-$ in the compound of formula (IV) depends on the acid used in a preceding diazotation step for providing the diazonium salt of formula (IV). For example, in case HCl is employed in the preceding diazotation step, the monovalent anion $X^-$ is $Cl^-$. Furthermore, if $H_2SO_4$ is used as the acid in the preceding diazotation step, the monovalent anion $X^-$ is $HSO_4^-$.

The above reaction for obtaining the compound of formula (V) from the diazonium salt of formula (IV) is carried out in a highly acidic medium, i.e. in an aqueous inorganic acid having a concentration of at least about 60%. The inorganic acid is a strong mineral acid. Suitable examples include e.g. $H_2SO_4$, HCl, HBr, or $H_3PO_4$.

In a preferred embodiment, the inorganic acid is $H_2SO_4$. The anion corresponding to deprotonated $H_2SO_4$, i.e., hydrogensulfate, is of low nucleophilicity. Therefore, when using $H_2SO_4$ as the acid, side reactions with the highly reactive diazonium salt of formula (IV) can be avoided and the resulting yield of 2,5-dihalogen phenols of formula (V) can be increased. When using $H_2SO_4$ as the inorganic acid, it is further advantageous to carry out the preceding diazotation step for obtaining the diazonium salt of formula (IV) using $H_2SO_4$. In these cases, $X^-$ is $HSO_4^-$. It is advantageous to use the same inorganic acid in both the diazotiation step for providing the compound of formula (IV) and the step of hydrolyzing the diazonium salt to provide the compound of formula (V) e.g. from the viewpoint of recycling the acid after completion of the reaction. Therefore, in a preferred embodiment of the invention, $H_2SO_4$ is used in both steps.

In prior art processes for hydrolyzing a diazonium salt of formula (IV) to obtain the phenol of formula (V) diluted inorganic acid, such as diluted $H_2SO_4$ is typically employed. By contrast, the step is carried out according to the invention in an aqueous inorganic acid having a high concentration, i.e. an aqueous inorganic acid such as $H_2SO_4$ having a concentration of at least 60%, more preferably at least 70%. Preferred concentration ranges of the $H_2SO_4$ in the diazonium salt hydrolysis step include about 60% to about 85%, more preferably about 70% to about 75%. In a preferred embodiment, the concentration of the $H_2SO_4$ in the diazonium salt hydrolysis step is about 72%. The inventors of the present invention have found that a high acidic medium in the step of hydrolyzing the diazonium salt of formula (IV) leads to higher yields, in particular if the resulting product of formula (V) is continuously removed from the reaction system.

The above step of obtaining the phenol of formula (V) from the diazonium salt of formula (IV) is carried out at a temperature of about 140° C. to about 250° C. This temperature is higher than typical temperatures employed in the prior art for hydrolyzing a diazonium salt of formula (IV) to obtain a phenol of formula (V). The present inventors have found that higher temperatures result in better yields, in particular when the resulting phenol is continuously removed from the reaction system. Thus, in preferred embodiments, the step is carried out at a temperature of at least about 150° C., more preferably at least about 160° C., and still more preferably about 170° C. Preferred temperature ranges for carrying out the diazonium salt hydrolysis step include about 150° C. to about 190° C., more preferably about 170° C. to about 180° C.

In an especially preferred embodiment, the above reaction step is carried out at the boiling point of the concentrated inorganic acid. For example, the reaction may be carried out at atmospheric pressure at a reaction temperature of about 140° C. and a concentration of aqueous $H_2SO_4$ of about 60% up to a reaction temperature of 250° C. and a concentration of aqueous $H_2SO_4$ of about 85%. In preferred embodiments, the reaction is carried out at atmospheric pressure at a reaction temperature of about 150° C. and a concentration of aqueous $H_2SO_4$ of about 65% up to a reaction temperature of 190° C. and a concentration of aqueous $H_2SO_4$ of about 75%. More preferably, the reaction may be carried out at atmospheric pressure at a reaction temperature of about 165° C. and a concentration of aqueous $H_2SO_4$ of about 70% up to a reaction temperature of 180° C. and a concentration of aqueous $H_2SO_4$ of about 73%. In a further preferred embodiment, the reaction is carried out at atmospheric pressure using aqueous $H_2SO_4$ having a concentration of about 72% and a reaction temperature of about 175° C.

As outlined above, it is a preferred embodiment of the present invention that in the diazonium salt hydrolysis step the resulting phenol of formula (V) is continuously removed from the reaction system. Furthermore, steam distillation is preferably employed for continuously removing the compound of formula (V) from the reaction system. Steam distillation is a separation technique known in the art that can be carried out on an industrial scale. For steam distillation, water is vaporized at elevated temperatures and the resulting water vapor (steam) is introduced into the reaction system. The steam is preferably heated to a temperature at least equal to the reaction temperature, preferably a higher temperature than the reaction temperature. In an embodiment of the invention, steam is injected into the reaction system at a temperature of about 140° C. or higher, preferably about 150° C. or higher, such as about 160° C. or higher, or about 170° C. or higher. In a preferred embodiment, steam is injected into the reaction system at a temperature of about 175° C. or higher.

According to preferred embodiments of the present invention, steam is continuously added to the reaction system in order to continuously remove the resulting product of formula (V). The reaction involving continuous steam addition can be carried out at reduced, elevated or atmospheric pressure. In one embodiment, the reaction is carried out at a pressure of about 80 to about 300 kPa, such as e.g. about 90 to about 200 kPa. In a preferred embodiment, the reaction is carried out at atmospheric pressure. As known in the art, the pressure usually referred to as "atmospheric pressure" is about 101.325 kPa. However, when using modified, i.e. elevated or reduced pressure for carrying out the reaction, the concentration of $H_2SO_4$ and the temperature can be varied, while still running the process at the boiling point of the system, as described in accordance with a preferred embodiment above. A person skilled in the art will be aware that to adapt the concentration of $H_2SO_4$, the reaction temperature and the pressure so as to arrive at a system at its boiling point. Illustrative embodiments are exemplified below.

For example, the reaction may be carried out at reduced pressure, i.e. a pressure lower than about 100 kPa, such as about 80 kPa, using a concentration of aqueous $H_2SO_4$ of about 75% or more at a temperature corresponding to the boiling point of the particular system employed, i.e. a temperature of lower than the corresponding boiling point at atmospheric pressure of 190° C. In this way, advantageously high concentrations of $H_2SO_4$ can be used, the efforts to provide high temperatures can be avoided, and still the process is carried out at the boiling point to improve efficiency of product removal through steam distillation.

Alternatively, the reaction may be carried out at elevated pressure, i.e. a pressure higher than about 100 kPa, such as up to about 300 kPa, using a concentration of aqueous $H_2SO_4$ of about 60% or more at a temperature corresponding to the boiling point of the system, i.e. a temperature of higher than the corresponding boiling point at atmospheric pressure of 140° C. In this way, higher reaction temperatures can be employed to improve reaction kinetics while efficient product removal at the boiling point of the system using steam distillation can be achieved.

After passing through the reaction system, the steam in admixture with the compound of formula (V) exits the reaction system through an outlet. The admixture of steam and 2,5-dihalogen phenol of formula (V) may be cooled to obtain phase separation. For example, the admixture steam and 2,5-dihalogen phenol may be cooled to about 50° C. to obtain two-phase system including a liquid aqueous phase and a liquid 2,5-dihalogen phenol phase. The liquid/liquid two-phase system can easily be separated using methods known in the art, e.g. in a water separator. Alternatively, the admixture of steam and 2,5-dihalogen phenol of formula (V) may be cooled to even lower temperatures to obtain a liquid water phase and a solid organic phase comprising of 2,5-dihalogen phenol. The solid phase comprising the 2,5-dihalogen phenol and the liquid water phase can easily be separated, using methods known in the art, such as filtration or centrifugation, to obtain crude product of formula (V). If desired, the crude product of formula (V) can be further purified e.g. using distillation. In this way, 2,5-dihalogen phenol can be obtained from the diazonium salt of formula (IV) in a continuous process in a yield of about 85% or more, preferably about 95% or more, such as about 98% or more.

The liquid water phase separated from the product of formula (V) can be extracted using a suitable organic solvent for obtaining residual 2,5-dihalogen phenol. Alternatively, the water phase separated from the solid product of formula (V) can be directly recycled for use in steam distillation e.g. in a closed water loop. According to the present invention it is preferred to employ the water phase obtained after separating the solid product of formula (V) directly for recycling in steam distillation in order to significantly reduce the waste material generated in the process. In a preferred embodiment, the water phase used for steam distillation can be recycled completely (i.e. except for the amount of water remaining in the crude product).

Methods for obtaining the diazonium salt of formula (IV) are not particularly limited according to the invention. In one embodiment, the compound of formula (IV) is provided by diazotating a compound of formula (III), wherein Hal is as defined above.

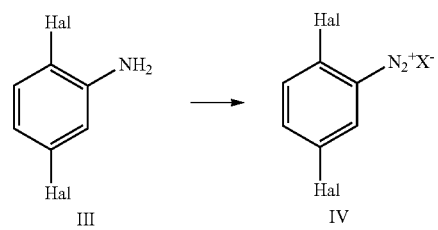

Reaction conditions for obtaining the compound of formula (IV) from 2,5-dihalogen substituted anilines of formula (III) are described above. In addition, this reaction step is well known in the art, and is employed in prior art reaction sequences for obtaining 2,5-dihalogen substituted phenols.

It is preferred to carry out the diazotation step using the same inorganic acid used in the diazonium salt hydrolysis step. In one embodiment, the diazotation step is carried out using $H_2SO_4$ as the inorganic acid. In another embodiment, $H_2SO_4$ is employed as the inorganic acid in both the diazotation step and the diazonium salt hydrolysis step.

The diazotation step for providing the compound of formula (IV) can be carried out according the present invention batch-wise or continuously. In a preferred embodiment, the diazonium salt of formula (IV) is continuously feed to the reaction system for hydrolyzing the diazonium salt for obtaining the phenol of formula (V). This can be accomplished e.g. by carrying out the diazotation step continuously. Alternatively, the diazonium salt may be prepared batch-wise and may be feed to the reactions system for hydrolyzing the diazonium salt from a reservoir.

In one embodiment, synthesis of diazonium salt is done by feeding 2,5-dihalogen aniline of formula (III) and $NOHSO_4$ to a reaction system comprising aqueous $H_2SO_4$ having a concentration of about 65%. $NOSO_4$ may be obtained e.g. by feeding $NO_x$ gas to sulfuric acid. 2,5-Dihalogen aniline of formula (III) may be added before, during or after feeding $NO_x$ to surfuric acid. The diazotation reaction may be carried out at a temperature of e.g. about 50° C. to about 60° C. The resulting product of formula (IV) is feed to the downstream reaction system for hydrolyzing the diazonium salt for obtaining the phenol as described above. Acid removed from the diazotation reaction system when feeding the diazonium salt to the downstream hydrolysis reaction system can be supplemented by adding $H_2SO_4$ to the diazotation reaction system as needed.

Thus, in one embodiment the present invention relates to a process in which in a first step 2,5-dihalogen aniline of formula (III) is diazotated to obtain a diazonium salt of formula (IV) which is feed to a downstream reaction system in which in a second step the diazonium salt of formula (IV) is hydrolyzed to obtain 2,5-dihalogen phenol of formula (V), wherein both steps are carried out using $H_2SO_4$ as the inorganic acid. In a preferred embodiment, the $H_2SO_4$ is at least in part recycled. For example, reaction medium based on highly concentrated $H_2SO_4$ may be removed from the reaction system for hydrolyzing the diazonium salt for obtaining the phenol. The $H_2SO_4$ removed from the reaction system can be recycled into in the diazotation reaction step or diazonium salt hydrolysis step. In this connection, the concentration of the $H_2SO_4$ to be recycled can be adjusted as desired. Adjusting to a desired concentration can be done e.g. by adding water or by adding concentrated $H_2SO_4$ or $SO_3$. Furthermore, the $H_2SO_4$ to be recycled can optionally be purified. Purification can be achieved e.g. by vacuum distillation or extraction with a suitable organic solvent. Suitable organic extraction solvents include e.g. ethers, such as tert.-butylmethyl ether, or halogenated solvents, such as chloroform or methylene chloride. In another embodiment, the $H_2SO_4$ to be recycled is re-used without purification.

In one embodiment, the $H_2SO_4$ is recycled into the diazotation step. According to one embodiment in this respect, residual 2,5-dihalogen phenol of formula (V) is optionally removed from the acid. This can be achieved e.g. by extracting with a suitable solvent as described above. It is generally not necessary to remove diazonium salt of formula (IV) or 2,5-dihalogen aniline of formula (III) from the acid. In another embodiment, the acid is recycled into the diazotation step without purification. The acid can be adjusted to the concentration required in the diazotation step by adding water. In this way, the $H_2SO_4$ can be recycled at least in part, e.g. more than 50%, such as about 60% of the $H_2SO_4$ can be recycled.

The method for obtaining the compound of formula (III), used in some embodiments according to the invention, is not particularly limited. The compound of formula (III) may for example be obtained by reducing a compound of formula (II) wherein Hal is as defined above.

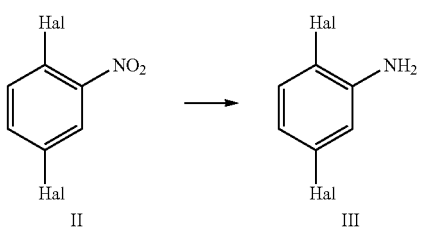

Suitable reaction conditions for this step are illustrated above and are known in the art. In fact, this step is employed in conventional reaction sequences for obtaining 2,5-dihalogen phenols.

Furthermore, the method for obtaining the compound of formula (II), employed in some embodiments of the present invention, is not specifically limited. In some embodiments, the compound of formula (II) is obtained by nitrating a compound of formula (I), wherein Hal is as defined above.

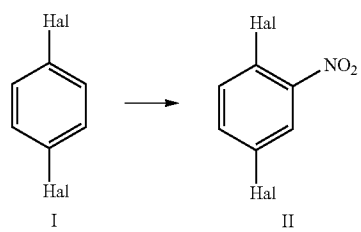

Suitable reaction conditions are described above and are known in the art. This step is employed in the art in conventional reactions sequences for obtaining 2,5-dihalogen phenols.

In a further embodiment, the compound of formula (V) is converted into valuable chemical products or intermediates. In a specific embodiment, the compound of formula (V) is subjected to a carboxylation reaction under Kolbe-Schmitt conditions to obtain a compound of formula (VI), wherein Hal is as defined above and $R^1$ is an alkali metal.

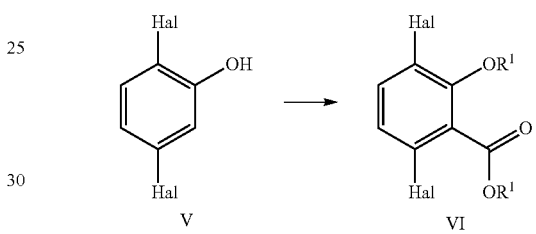

In the carboxylation step, the compound of formula (V) is first converted into the corresponding phenolate by treating with an alkali metal hydroxide $R^1OH$. $R^1OH$ can be sodium hydroxide or potassium hydroxide, e.g. potassium hydroxide. The alkali metal hydroxide can be used in about stoichiometric amounts in an aqueous solution having e.g. a concentration of 50 wt.-%. The conversion can be carried out in a suitable organic solvent such as xylene. Water can be removed from the system using azeotropic distillation.

Subsequently, the phenolate is contacted with gaseous $CO_2$ under high pressure. The phenolate solution in e.g. xylene can be used without further workup. The reaction affords the carboxylic acid salt of formula (VI), which normally is not soluble in the reaction medium such as xylene but is soluble in water and, therefore, can easily be separated.

In a further embodiment, the compound of formula (VI) is alkylated to obtain a compound of formula (VII).

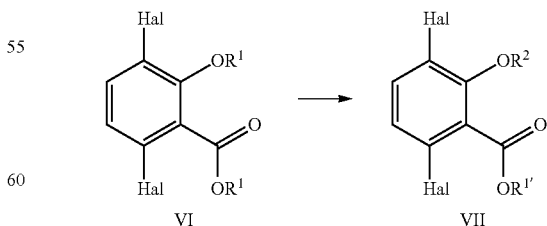

The reaction is accomplished by reacting the compound of formula (VI) with an alkyl halide of formula $ZR^2$, wherein Z is halogen, such as Cl, Br or I, and $R^2$ is as defined above. In particular, Z can be Cl or Br, e.g. Cl. In one embodiment, the alkyl halide is methyl chloride. The reaction can be carried out in aqueous solution. During the reaction, the pH, temperature and pressure may be controlled such that the reaction is carried out at a pH of 8 to 12, a temperature of about 90° C. to about 100° C. and/or a pressure of about 500 to about 1050 kPa. An excess of alkyl halide is usually used. Thus, the compound of formula (IV) can be partly esterified. In this case, $R^{1'}$ is identical to $R^2$.

Furthermore, if deemed appropriate to increase solubility of the compound of formula (VI), the double salt may be converted in advance of the reaction to a corresponding mixed salt by treating with an alkali metal hydroxide different from the alkali metal hydroxide used in the previous reaction step. For example, when potassium hydroxide is used in the Kolbe-Schmitt reaction step, the compound of formula (VI) may be treated with sodium hydroxide in advance of the alkylation step to obtain a mixed potassium/sodium salt. In these cases, $R^{1'}$ may be an alkali metal different from $R^1$. In other cases, $R^{1'}$ can be identical to $R^1$.

In a further embodiment, the compound of formula (VII) is converted to the compound of formula (VIII).

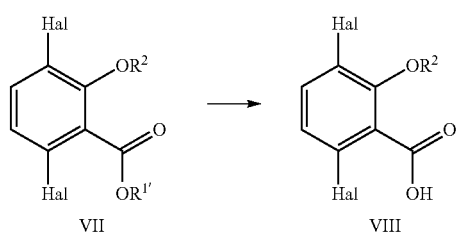

In cases where the compounds of formula (VII) include an ester in which $R^{1'}$ is identical to $R^2$, the ester can be hydrolyzed under basic conditions using a suitable base to obtain the corresponding carboxylic acid salts. For example, alkali metal hydroxides such as NaOH may be employed here. Compounds of formula (VII) in which $R^{1'}$ is an alkali metal may be present during hydrolysis without harm. Thus, a composition comprising a compound of formula (VII) in which $R^{1'}$ is an alkali metal, such as sodium, is obtained.

The alkali metal salt of formula (VII) can then be acidified in solution using a suitable acid, such as $H_2SO_4$ or HCl, e.g. HCl, to afford the compound of formula (VIII). In cases where a compound of formula (VII) in which $R^{1'}$ is an alkali metal is obtained in the previous reaction step, the composition can be directly subjected to acidification without the above hydrolyzation.

Although the processes according to the embodiment as described above can be employed for providing a variety of final products and intermediates, the present invention will be illustrated by describing a sequence of reaction steps for obtaining dicamba starting from 1,4-dichlorobenzene. A person skilled in the art will comprehend that certain reaction steps in this sequence are preferred as opposed to essential, and will further be able to adapt the processes described herein for the production of other compounds and intermediates within the scope of the appended claims.

In an especially preferred embodiment, the present invention provides a process for obtaining dicamba starting from 1,4-dichlorobenzene or any other suitable intermediate described herein. In a first step of the reaction sequence, 1,4-dichlorobenzene is subjected to nitration as described above to obtain 2,5-dichloro nitrobenzene.

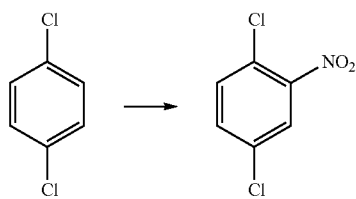 [SMILES: Clc1ccc(Cl)cc1 ; O=[N+]([O-])c1cc(Cl)ccc1Cl]

1,4-dichlorobenzene is a compound within the definition of formula (I) as defined above, in which Hal is in both instances Cl. Furthermore, 2,5-dichloro nitrobenzene is a corresponding nitrated derivative thereof within the definition of the above formula (II).

In a further reaction step of the most preferred reaction sequence according to the present invention, 2,5-dichoro nitrobenzene is subjected to reduction as described above to obtain 2,5-dichloroaniline.

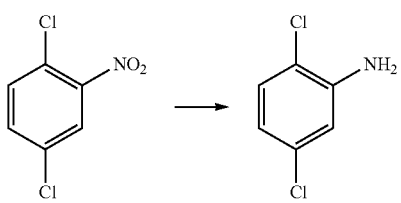 [SMILES: O=[N+]([O-])c1cc(Cl)ccc1Cl ; Nc1cc(Cl)ccc1Cl]

2,5-dichloroaniline is a compound according to formula (III) according to the present invention, in which Hal is in both instances Cl.

The preferred reaction sequence according to the present invention includes a further step of diazotating 2,5-dichloroaniline in $H_2SO_4$ in the presence of a diazotating agent such as $NOHSO_4$ to obtain 2,5-dichlorobenzenediazonium hydrogensulfate.

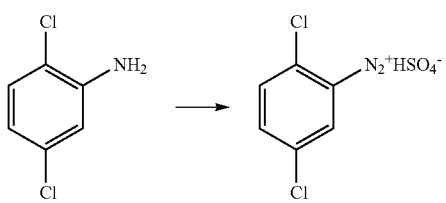

2,5-dichlorobenzenediazonium hydrogensulfate is a compound within the definition of formula (IV) according to the present invention, in which Hal is in both instances Cl and $X^-$ is $HSO_4^-$. The reaction can be carried out as generally described above.

In a further reaction step according to the preferred reaction sequence of the invention, 2,5-dichlorobenzenediazonium hydrogensulfate is hydrolyzed to obtain 2,5-dichlorophenol.

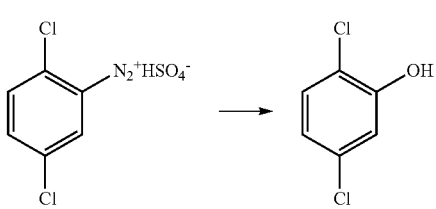

2,5-Dichlorophenol is a compound of formula (V) according to the invention in which Hal is in both instances Cl. As outlined above, the diazonium salt hydrolysis step is carried out at higher temperatures, i.e. at a temperature of about 140° C. to about 250° C., preferably at a temperature of at least about 150° C., more preferably at least about 160° C., still more preferably at least about 170° C., and most preferably about 170° C. to about 180° C. In a further preferred embodiment, the 2,5-dichlorophenol is continuously removed from the reaction mixture via a steam distillation.

According to preferred embodiments of the invention, 2,5-dichlorophenol is further subjected to carboxylation under Kolbe-Schmitt conditions using KOH and $CO_2$ as described above to obtain the dipotassium salt of 3,6-dichlorosalicylic acid.

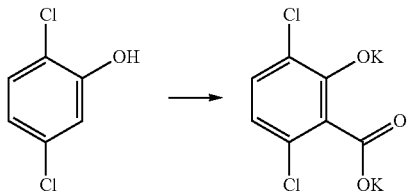

The dipotassium salt of 3,6-dichlorosalicylic acid is a compound according to formula (VI) of the present invention, in which Hal is in both instances Cl, and $R^1$ is K.

It is further preferred that the dipotassium salt of 3,6-dichlorosalicylic acid is methylated in a subsequent reaction step using methyl chloride. As described above, this conversion may include converting the dipotassium salt into a mixed salt in order to improve solubility in water. In a preferred embodiment, NaOH is used for the provision of the mixed salt. In view of this, methylation of dipotassium 3,6-dichlorosalicylic acid after conversion into a mixed salt affords typically a mixture of the sodium and/or potassium form of 3,6-dichloro-2-methoxybenzoic acid and 3,6-dichloro-2-methoxybenzoic acid methyl ester.

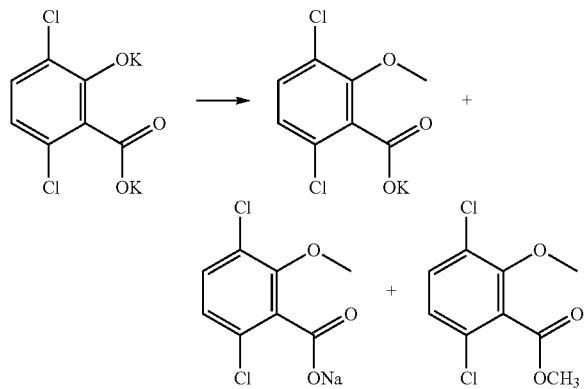

The product obtained in the reaction is a compound according to formula (VII) of the present invention in which Hal is in both instances Cl, $R^2$ is methyl, and $R^{1'}$ is either K, Na or methyl.

The above mixture is subsequently preferably converted to dicamba by hydrolyzing the ester compounds in the mixture using NaOH as described above and subsequently acidifying the resulting product using HCl as outlined above.

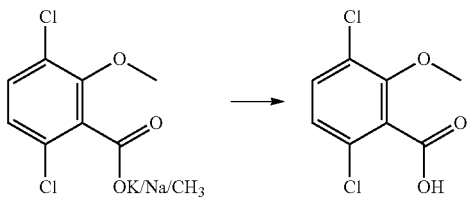

Dicamba is a compound according to formula (VIII) of the present invention, in which Hal is in both instances Cl, and $R^2$ is methyl.

The above reaction sequence can be carried out on an industrial scale with good yields. The starting materials required for the reactions sequence including 1,4-dichlorobenzene are readily available at low costs. Thus, in a preferred embodiment, the present invention provides an advantageous synthetic route to dicamba for production on industrial scale with improved yields starting from readily available 1,4-dichlorobenzene.

EXAMPLES

Working Example 1

Diazotation of 2,5-dichloroaniline was done by adding within a period of 30 minutes 145.8 g 2,5-dichloroaniline (4.67 mol) at 60° C. to about 739.3 g of aqueous $H_2SO_4$ having a concentration of 62% to obtain the corresponding 2,5-dichloroaniline hydrogensulfate in the form of a suspension. After cooling to 50° C. 285.9 g of 40% nitrosylsulfuric acid (0.9 mol) were added within one hour. The reaction mixture was stirred for an additional hour. Then, the reaction mixture was heated to 150° C. to 155° C., while the resulting 2,5-dichlorophenol was continuously removed using steam distillation. The water phase was separated from the distillate in a water separator and was continuously recycled for use in steam distillation. Steam distillation is terminated after nitrogen formation can be no longer observed. Crude 2,5-dichlorophenol in an amount of 127.7 g is obtained. The final yield is 81%.

Working Example 2

Diazotation was carried out analogously to example 1 using 18.1 g (0.112 mol) of 2,5-dichloroaniline. Then, hydrolysis to obtain 2,5-dichlorophenol was done under reflux (145° C. to 150° C.) until nitrogen formation was no longer observed. Afterwards, the obtained 2,5-dichlorophenol was removed using steam distillation. The yield of 2,5-dichlorophenol is 75%.

Working Example 3

Diazotation of 2,5-dichloroaniline was done by adding 40.5 g 2,5-dichloroaniline (0.25 mol) at 60° C. to about 200 g of aqueous $H_2SO_4$ having a concentration of 60% to obtain the corresponding 2,5-dichloroaniline hydrogensulfate in the form of a suspension. After cooling to 50° C. 79.5 g of 40% nitrosylsulfuric acid (0.25 mol) were added within one hour. The reaction mixture was stirred for an additional hour. The obtained diazonium salt is used without further isolation to provide 2,5-dichlorophenol.

The mixture obtained above was added over two hours to about 300 g $H_2SO_4$ having a concentration of 65% at a temperature of 150° C. Resulting 2,5-dichlorophenol was continuously removed from the reaction system using steam distillation. During this, crude 2,5-dichlorophenol was isolated from the water used for steam distillation in a water separator. Water was recycled for steam distillation. The obtained yield of 2,5-dichlorophenol is 88%.

Working Example 4

Diazotation of 2,5-dichloroaniline was done as described in example 1 except that 81 g 2,5-dichloroaniline (0.5 mol) were added to about 301 g aqueous $H_2SO_4$ having a concentration of 65% (molar ratio $H_2SO_4$:2,5-dichloroaniline about 4:1).

The above mixture was added over a period of four hours to about 820 g $H_2SO_4$ having a concentration of 72% at a temperature of 175° C. Simultaneously, steam distillation was carried out in a closed water loop. Distillate containing 2,5-dihlorophenol and water was condensed at 50° C. and the obtained water phase was separated and recycled for steam distillation. The obtained yield of 2,5-dichlorophenol is 98.8%.

Working Example 5

A gaseous mixture of $NO_2$ and NO (about 1:1) is fed into a suspension of 32.5 g 2,5-dichloroaniline in 98.9 g 98% sulfuric acid. In order to mimic nitrogen oxide industrial waste gases, the mixture of $NO_2$ and NO was prepared by reacting copper flakes at −5° C. to 0° C. with 60% nitric acid. After $NO_x$ formation, the mixture was diluted with some water and heated to reflux. An oil was formed which could be identified by means of $^1$H-NMR as 2-5-dichlorophenol.

The invention claimed is:

1. A process for reacting chemical compounds comprising the step of hydrolysing a compound of formula (IV)

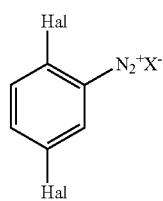

IV wherein Hal is independently selected from the group consisting of Cl and Br, and $X^-$ is $HSO_4^-$,
in the presence of an aqueous inorganic acid, wherein the aqueous inorganic is $H_2SO_4$, which has a concentration of at least 60% by weight, at a temperature of 140° C. to 250° C., to obtain a compound of formula (V)

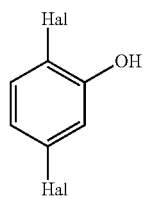

V wherein Hal is as defined above;
and wherein the compound of formula (IV) is provided by diazotating a compound of formula (III)

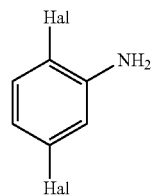

III wherein Hal is as defined above;
and wherein the step of diazotating the compound of formula (III) to obtain the compound of formula (IV) is carried out in $H_2SO_4$ having a concentration of at least 40% by weight in the presence of $NOHSO_4$, and wherein the temperature is from 45° C. to 65° C.

2. The process of claim 1, wherein product of formula (V) is continuously removed from the reaction system using steam distillation.

3. The process of claim 1, wherein the concentration of the $H_2SO_4$ in the hydrolysis step is at least 70% by weight.

4. The process of claim 3, wherein at least part of the $H_2SO_4$ used in the hydrolysis step is recycled.

5. The process of claim 1, wherein the hydrolysis step is carried out at a temperature of at least 160° C.

6. The process of claim 1, wherein NO$\underline{H}$SO$_4$ is obtained by feeding $NO_x$ gas to sulfuric acid having a concentration of at least about 60% by weight, and wherein the $NO_x$ gas is a mixture of NO and $NO_2$ in a molar ratio of about 1:1.

7. The process of claim 1, wherein the water used for steam distillation is recycled in a closed water loop.

8. The process of claim 1, wherein the compound of formula (III) is obtained by reducing a compound of formula (II)

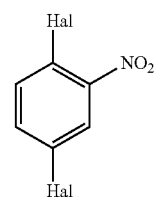

II wherein Hal is independently selected from the group consisting of Cl and Br.

9. The process of claim 8, wherein the compound of formula (II) is obtained by nitrating a compound of formula (I)

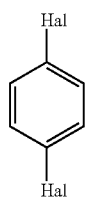

I wherein Hal is independently selected from the group consisting of Cl and Br.

10. The process of claim 1, further comprising the step of reacting the compound of formula (V) to obtain a compound of formula (VI)

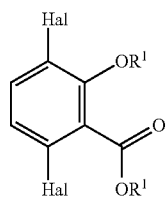

VI wherein Hal is independently selected from the group consisting of Cl and Br, and $R^1$ is an alkali metal.

11. The process of claim 10, wherein the step of reacting the compound of formula (V) to obtain a compound of formula (VI) is carried out in the presence of an alkali metal hydroxide and carbon dioxide.

12. The process of claim 10, further comprising the step of reacting the compound of formula (VI) to obtain a compound of formula (VII)

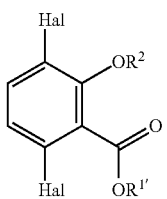

VII wherein $R^2$ is —$(C_1-C_4)$alkyl, $R^{1'}$ is an alkali metal or —$(C_1-C_4)$alkyl, and Hal is independently selected from the group consisting of Cl and Br.

13. The process of claim 12, further comprising the step of reacting the compound of formula (VII) to obtain a compound of formula (VIII)

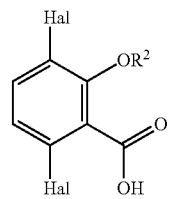

VIII wherein $R^2$ and Hal are as defined in claim 12.

14. The process of claim 12, wherein
(a) Hal is Cl; and/or
(c) $R^{1'}$ is selected from the group consisting of sodium and potassium, or $R^{1'}$ is selected from the group consisting of ethyl and methyl; and/or
(d) $R^2$ is selected from the group consisting of ethyl and methyl.

15. The process of claim 13, wherein the compound of formula (VIII) is

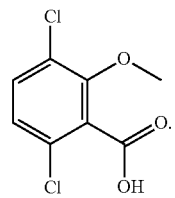

* * * * *